United States Patent [19]
Holden et al.

[11] Patent Number: 6,131,072
[45] Date of Patent: Oct. 10, 2000

[54] LANE TRACKING SYSTEM AND METHOD

[75] Inventors: David P. Holden, Menlo Park; Andrew L. Diamond, San Diego, both of Calif.

[73] Assignee: PE Applied Biosystems, a division of Perkin-Elmer, Foster City, Calif.

[21] Appl. No.: 09/017,977

[22] Filed: Feb. 3, 1998

[51] Int. Cl.[7] .................................................. G01N 21/00
[52] U.S. Cl. ............................ 702/20; 702/19; 702/22; 702/27; 702/32; 204/450; 204/461; 204/600; 356/344
[58] Field of Search .............................. 702/20, 19, 22, 702/27, 32; 204/461, 450, 600; 356/344

[56] References Cited

U.S. PATENT DOCUMENTS 4,837,687  6/1989  Tanaka et al. ........................ 204/461
4,885,697  12/1989  Hubner ................................. 702/27

Primary Examiner—Marc S. Hoff
Assistant Examiner—Hien Vo
Attorney, Agent, or Firm—David J. Weitz; Wilson Sonsini; Goodrich & Rosati

[57] ABSTRACT

A system and method for identifying lanes in images generated from DNA sequencing and fragment analysis is described. One example method includes a computer implemented method of determining the locations of lanes of separated samples. Each lane corresponds to a sample being separated by flowing the sample through a media. The method includes the following elements. Place some samples on the media. Cause the samples to separate into the lanes. Create a digital image of the lanes. Fit some curves to the lane images. Each curve corresponds to a lane formed from a separated sample.

38 Claims, 12 Drawing Sheets

LANE TRACKING SYSTEM AND METHOD

1. THE BACKGROUND OF THE INVENTION a. The Field of the Invention

This invention relates to the field of processing materials to determine their constituent components. In particular, the invention relates to automatically identifying lanes of separated sample materials.

b. Background Information

Gel electrophoresis, and other molecular separation techniques, allow scientists to determine the molecular sequence of biological materials. For example, gel electrophoreses is used to determine the DNA sequence of a given sample of biological matter. DNA sequencing involves determining the sequence of nucleotides that form the DNA.

Generally, gel electrophoresis involves placing a gel material on a glass plate. The gel has a number of wells at one end of the plate. These wells are filled with the sample of the biological material and a number of dyes. When excited with light, the dyes fluoresce. The samples react with the dyes to make partial copies of samples. Each partial copy contains from 1-N nucleotides of the DNA sequence of the sample (where N is the number of nucleotides in the sample). Thus, each partial copy has a weight proportional to the number of nucleotides in that copy. A goal of gel electrophoresis is to separate the partial copies in order of their weight. The type of dye at the end of each partial copy indicates the type of the last nucleotide in that partial copy. The type of dye can be determined from the dye's fluorescent color. The glass plate is placed between two poles of an electric field. Under the effects of the magnetic field, the partial copies move through the gel. The partial copies move at rates proportional to their weights. Thus, longer partial copies move more slowly than shorter partial copies. The partial copies separate according to their weight, and therefore, length. The separated partial copies separate into lanes of bands, each band corresponding to a different length of partial copy. By reading the color of the bands in order, the DNA sequence can be determined.

Automated computer systems have been developed that automatically locate the lanes, and ultimately the bands in images of the gels. The band information is what is important to the scientist. However, to identify the bands, the lanes must be accurately identified. An example of a system that used alpha-beta tracking is the Sequence Analysis™ system available from PE Applied Biosystems, Inc. However, many of these systems do not work well for some gel images. The problem arises with the inconsistent shape of the lanes produced in the gels. For example, the lanes of bands are not necessarily straight; they may veer off to one side of the gel or the other.

One example of a previous system used a technique called alpha-beta tracking. In alpha-beta tracking, a program would start with what it thought were two bands in a lane. The program then finds the direction of flow between those two bands. The program then projects out a probability field of where a subsequent band in the lane should be. The corresponding area in the gel image is then searched for a band. The program then selects a band in that area as being the most likely next band in the lane. The process repeats until the end of the lane is reached. The problem with alpha-beta tracking is that two bands can fall within the probability area. In certain circumstances, alpha-beta tracking will select the wrong band. Once the wrong band is selected, the correct lane will not be identified.

Alpha-beta tracking performs particularly poorly in some applications of gel electrophoresis, such as gene scanning (e.g., STR analysis). In gene scanning, the lanes may have large gaps between bands. (For comparison, in DNA sequencing, long lines of bands appear in the lanes. Generally, there is a band in a lane for each possible length of a partial copy of the DNA matter.) In gene scanning applications, there may be many large gaps between bands in a lane. The relatively few number of bands makes the automatic tracking of the lanes difficult and often causes previous systems to require human intervention to identify lanes.

The problem of requiring human intervention for lane identification is that it increases the cost of processing gels and also decreases the through put of the systems. The need for human intervention can become the bottleneck in some situations. Also, as the number of lanes per gel increases and the number of runs per day increases, the problem compounds.

Therefore it is desirable to have an improved automated process for determining where the lanes are in a gel of samples. The process should recognize a higher percentage of lanes than presently available systems. Additionally, where a human is still required to identify lanes, the system should provide an improved interface so that less intervention is required.

2. A SUMMARY OF THE INVENTION

A system and method for identifying lanes in images generated from DNA sequencing and fragment analysis is described.

One embodiment of the invention includes a computer implemented method of determining the locations of lanes of separated samples. Each lane corresponds to a sample being separated by flowing the sample through a media. The method includes the following elements. Place some samples on the media. Cause the samples to separate into the lanes. Create a digital image of the lanes. Fit some curves to the lane images. Each curve corresponds to a lane formed from a separated sample.

The lanes have bands of separated samples. The image of these bands can be used to identify the lanes. For example, in some embodiments, a pattern recognition system finds the centers of the bands. This center information can then be used to determine the approximate distances between adjacent lanes and the general direction of flow of the lanes, which can be used to fit the curves to the lane images. The use of the pattern recognition system helps improve the overall performance of the system because it helps better identify the location of bands within lanes.

In some embodiments, an initialization process involves the computer making an initial guess at the number and location of the lanes. This initial guess is then interatively refined until a sufficiently good match is made.

In some embodiments, local and/or global optimization processes are used to fit the curves to the lanes. In the local optimization, individual curves are iteratively adjusted using definitions of the appropriate amount of movement. The definitions can use information like the relative location of that curve to a center of a band. The local optimization helps improve the speed of the lane tracking system by quickly providing the computer with a good approximate fit. The global optimization process attempts to maximize the fit of all of the curves to all of the lanes. The fit is determined by rules such as how close lanes should be an a given area, and what the general shape of a lane should be. The global optimization helps provide a good fit for all of the curves. Importantly, the global, and to some extent the local, optimizations use information about the overall look of the lanes in the media. This overview information significantly improves the lane tracking results, as compared to other systems.

Although many details have been included in the description and the figures, the invention is defined by the scope of the claims. Only limitations found in those claims apply to the invention.

3. A BRIEF DESCRIPTION OF THE DRAWINGS

The figures illustrate the invention by way of example, and not limitation. Like references indicate similar elements.

In FIG. 9, the results of a DNA sequencing process are shown with the lanes being tracked.

4. THE DESCRIPTION a. Overview of the Description

The following describes how the description is presented. First, a definitions section provides definitions for terms used in the description. Next, a number of sections describe various embodiments of the invention. Generally, where a section describes a figure other than a flowchart, the section has the following format. First, all of the elements of the figure are listed. Next, the interconnections of the elements are described. Finally, their interactions and operations are described. In some cases, alternative or additional embodiments are described. Additionally embodiments are also described in a separate section. The last section is the conclusion.

b. Definitions

This section describes some terms that are used in the description.

Sample—any bio-molecule that can be separated using any of a number of separation techniques.

Bio-molecule—any of a number of biological molecules such as DNA, RNA, proteins, etc.

Curves, Splines, Model Lanes—all refer to data structures used to identify and track lanes in the gels.

Lane—refers to the lanes formed in the gels by the separations of the samples. However, lane also refers to the data structures used to identify and track lanes. The context of the use will make clear whether the word is referring to the data structure or the actual lane in the gel.

c. Overview of an Embodiment of the Invention

This section describes an example embodiment of the invention. In one embodiment, a computer examines a digital image of a gel to identify the lanes of separated DNA in the gel. Each lane has fluorescent bands corresponding to particular fragments of the DNA. The computer first analyzes the digital image to find the centers of the bands. The centers of the bands help the computer track the lanes. The computer then uses information about the general nature of what lanes should look like, and information about the approximate spacing and directions of lanes, to fit a set of splines to the lane images in the digital image.

One of the insights in developing this embodiment is that there is a significant amount of information in the global view of the lanes that had not been used in previous systems. When humans exam gel images they use the general look of all of the lanes to identify a particular lane. For example, if a group of lanes on one side of a gel generally veer off to the left, a person can see this and use this information to identify lanes in that area of the gel. This type of overall view information is used in this embodiment of the invention.

d. System View

Figure 1:
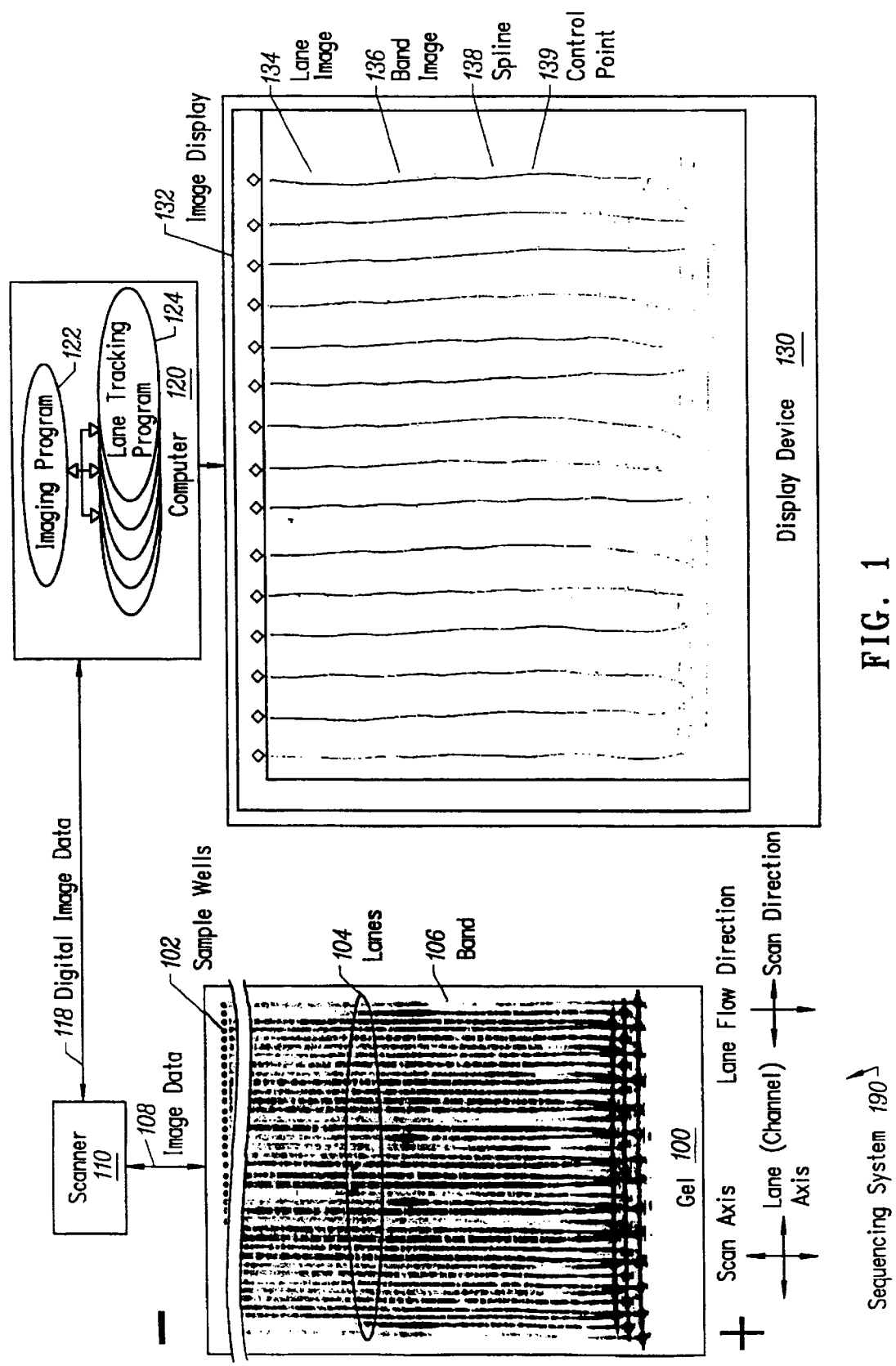
FIG. 1 illustrates a system for tracking lanes in a gel as may be used in one embodiment of the invention.

This section describes the system of FIG. 1 which can be used for tracking lanes in a gel as may be used in one embodiment of the invention.

FIG. 1 includes a sequencing system 190. The sequencing system 190 includes a gel 100, a scanner 110, a computer 120, and a display device 130. The gel 100 includes a number of sample wells 102, some lanes 104, and a band 106. The computer 120 includes an imaging program 122 and a number of other programs. These other programs include a lane tracking program 124. The display device 130 is displaying an image display 132. The image display 132 includes a lane image 134, a band image 136, a spline 138, and a control point 139.

The following describes interconnections between the elements of FIG. 1. The gel 100 provides image data 108 to the scanner 110. The scanner 110 provides digital image data 118 to the computer 120. The imaging program 122 controls the various programs used in processing the digital image data 118. One of these programs includes the lane tracking program 124. The computer generates data for the image display 132 on the display device 130.

The following describes the elements and their interactions in greater detail. The gel 100 represents a glass plate coated with a gel material. The gel material provides a medium through which sample material, in the sample wells 102, can travel. The sample material moves through the gel 100 as a result of electric field applied across the gel 100. The result of the samples traveling is a number of separated lanes, such as lanes 104. Each lane corresponds to a different sample well of the sample wells 102. The lanes are made up of a number of bands, such as band 106.

Importantly, the sample wells 102 may not all be loaded with sample material. Also, during the separation, not all of the lanes 104 are straight. This makes automatic detection of the lanes difficult.

The scanner 110 scans the gel 100 to capture the image of the gel 100. The scanner converts this analog image data 108 into the digital image data 118. The digital image data 118 represents a digital image of the gel 100.

The computer 120 represents any of a number of computer systems. Example computer systems include Mac OSTM™ computer systems available from Apple Computer Inc, PC compatible systems, Unix workstations, and can include one or more computers (e.g., such as a network of computers). What is important is that the computer 120 have the capability to process images. To process images, the computer 120 includes a memory and a processor.

The imaging program 122, being run by the computer 120, typically controls the scanner 110 to cause the scanner 110 to provide the digital image data 118. The computer 120 can also control the electric field applied across the gel 100. However, what is important is that a digital image is received by the image program 122. This digital image data 118 includes images of lanes with bands. For example, the digital image data 118 includes a lane image 134. The lane image 134 includes a number of bands including the band image 136.

In some embodiments of the invention, the imaging program 122 and/or the lane tracking program 124 can a be included in a computer program product. The computer program product can be a floppy disk, a CD ROM, a DVD disk, a zip disk, a hard disk, or some other computer program product.

The imaging program 122 controls the lane tracking program 124. The lane tracking program 124 tracks the lane images in the digital image data 118. In this example, the lane tracking program 124 has fit a number of splines to the various lane images. As can be seen by the image display 132, the splines generally run through the center of the lane images. For example, the spline 138 runs approximately through the middle of the lane image 134. This is the case even though the lane image 134 is not a straight lane. The lane image 134 veers significantly towards the left at the bottom of the image display 132. Importantly the lane tracking program 124 was able to fit the spline 138 to the lane image 134 even though the lane image 134 is not oddly shaped.

In some embodiments of the invention, the imaging program 122 provides a user interface by which a user can modify any of the tracking of the lanes. This is helpful where automatic extraction of the DNA sequences are achieved by other programs in the imaging program 122. The user interface presents the user with a number of control points per lane, such as control point 139. The user can change the location of the control points. These control points change the shape of the corresponding spline. For example, modifying the control point 139 will modify the shape of the spline 138. Additionally, in some embodiments, changing the location of a control point will cause a corresponding change in the shape of the neighboring splines. This is done using the global optimization process described below. Thus, the user can change the shape of a number of splines automatically.

For the purposes of this description, some coordinate axes are defined. FIG. 1 shows the scan direction and the lane flow direction. The scan direction is perpendicular to the lane flow direction. The axes defined by the scan direction and the lane flow direction are also defined. The scan direction defines the scan axis as being perpendicular to the scan direction. Similarly, the lane axis (or channel axis) is defined as being perpendicular to the lane flow direction.

The following sections describes the use of the lane tracking program 124 to track the lane images.

e. Example Method of Tracking Lanes

Figure 2:
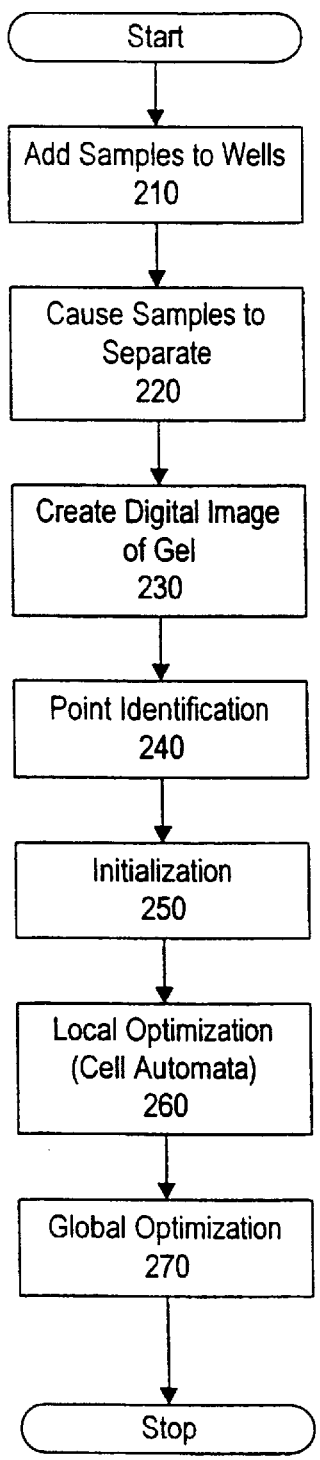
FIG. 2 illustrates an embodiment of a method of tracking lanes in a gel as may be used in the system of FIG. 1.

FIG. 2 illustrates an embodiment of a method of tracking lanes in a gel as may be used in the system of FIG. 1. The following describes the use of the lane tracking program 124 in the context of reading the DNA sequence in the gel 100.

At block 210, a scientist adds samples to the wells 102. The samples include DNA material and some fluorescent dyes. U.S. patent application Ser. No. 08/642,330, entitled "Energy Transfer Dyes With Enhanced Fluorescence," filed May 3, 1996, and having inventors Linda G. Lee, Sandra L. Spurgeon, and Barnett Rosenblum, assigned to the assignee of the present invention, describes a number of energy transfer dyes with enhanced fluorescence for use in, among other applications, gel electrophoresis. The dyes in the DNA samples react such that the dyes make partial copies of the DNA samples.

At block 220, the electric field is applied across the gel 100. This causes the samples, in particular the partial copies of the samples, to separate. These samples travel though the gel 100 and separate into the various bands for each lane. The computer 120 can control the application of the electric field, in some embodiments.

At block 230, the scanner 110 captures the image of the gel 100. This can be accomplished in any number of ways. For example, the scanner 110 can excite the lanes and then sense any fluorescence from the dyes. Fluorescence intensity values and colors are then recorded as the digital image data 118.

The imaging program 122 invokes a lane tracking program 124. The lane tracking program has two main phases. The first phase identifies points in the digital image data 118 that correspond to bands. The next phase connects the bands using splines using a spline fitting technique.

Block 240 represents the first phase. At block 240, point identification identifies the points corresponding to the bands in the digital image data 118.

The second phase, referred to as "connecting the dots", includes block 250 through 270. Its task is to track the lanes, i.e. fit the splines, as indicated by the points found in the first phase. The splines are fit to the data points by optimization processes that move the splines such that they correspond to the lanes.

At block 250, some initialization steps are taken. Most notably the compression of the image along the scan axis. Next at block 260, the center portion of the image (i.e. the center scans) is tracked. This is accomplished using a boot strapping process which employs successive invocations of a local optimization process. The boot strapping process is elaborated below. Each invocation of the local optimization tracks additional lanes. One example of local optimization employed is "cell automata", which is elaborated below. After the center scans are tracked by local optimization, the entire image is tracked by global optimization at block 270. The global optimizer is a modified version of the Metropolis simulated annealing algorithm. The global optimizer is called twice. It is run for two epochs at twenty-five batches per epoch. For the first time, the global optimization is run for two epochs at twenty-five batches per epoch. Epochs and batches relate to the simulated annealing process used by the global optimization. This process is described in greater detail below. If the results of the first run are evaluated as being particularly good, then the global optimization is run for one epoch of ten batches, at very low energy. Otherwise, three epochs at a high starting temperature are run.

After the global optimization, the results of the spline fitting can be displayed on the display device 130.

f. Example Method of Identifying Band Centers

Figure 3:
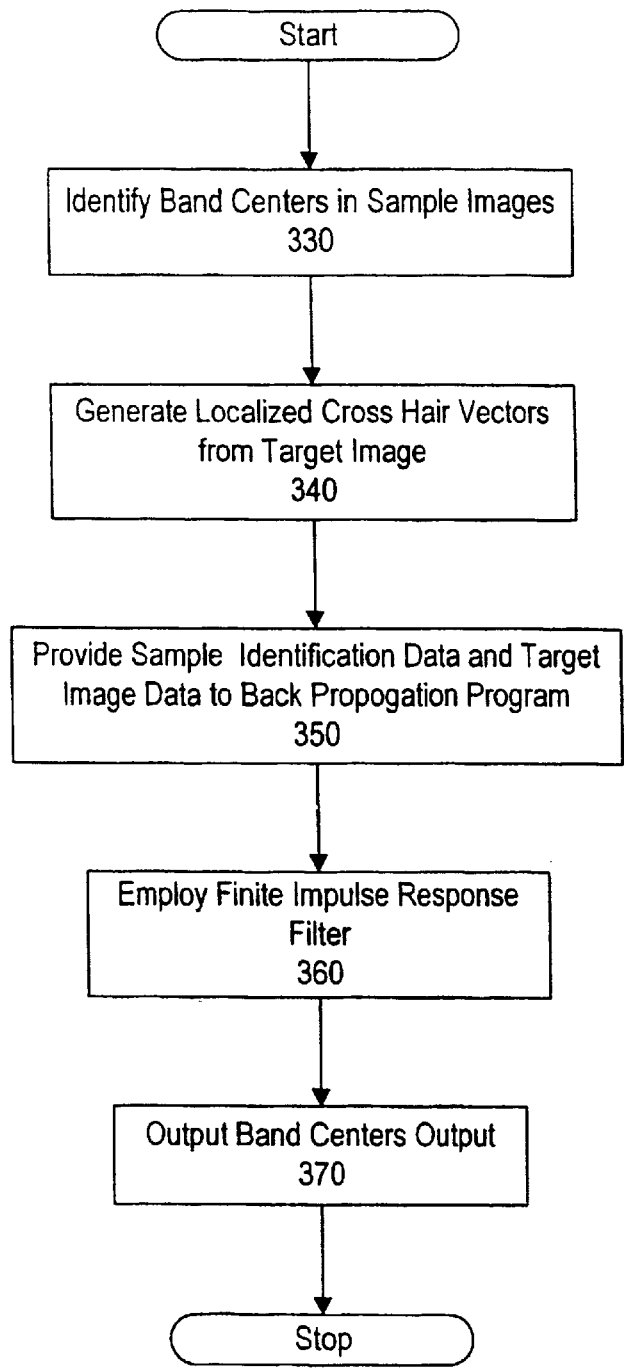
FIG. 3 illustrates an embodiment of a method of identifying the center of bands.

FIG. 3 illustrates one embodiment of a method of identifying the approximate centers of bands. The ultimate goal of the example method is to provide the lane tracking program 124 with the locations of the centers of bands in the digital image data 118. Additionally, the confidence value associated with any band identified by this technique is also generated.

The point identification process is important in the overall curve fitting process. The reason for this is that the point identification process provides a superior indication of the location of the center of bands in the digital image data 118. This improves the reliability of the curve fitting process.

Previously systems used a point identification technique that would simply take highest intensity value of a band as the center of the band. A problem with this approach is that the highest point of a neighbor may bleed into a adjacent band. Using alpha-beta tracking technique would cause the tracker begin tracking the adjacent lane. Using the technique of FIG. 3, the system can identify the center of many different types of bands, including bands where neighboring bands have bled into a particular band.

Generally, the technique of FIG. 3 involves using a pattern recognition system. The pattern recognition system has been trained to identify the center of bands in sample pictures. The training data is supplied to a back propagation process along with the digital image data 118. The results are an image with non-zero intensity values at locations where the center of bands are believed to exist. The intensity value of each non-zero point value indicates the confidence level that a particular point represents the center of a band.

The embodiment of FIG. 3 is now described in greater detail.

At block 330, a programmer identifies the band centers in one or more sample images. This is done by a person who takes a number of sample gel images and locates the centers of the bands in those images. The lane tracking program 124 keeps track of this training information.

At block 340, the lane tracking program 124 generates localized cross hair vectors from the digital image data 118. Generating localized cross hair vectors is a known technique. Generally, it involves converting a two-dimensional image with intensity values into a one-dimensional image with intensity values.

At block 350, the cross hair vectors are provided, along with the sample identification data generated at block 330, to the back propagation program. Back propagation, as noted above, is a known technique used for image recognition.

As part of the back propagation program 360, a finite impulse response filter is used. The coefficients for the finite impulse response filter are derived from the sample identification data. The cross hair vectors are used as inputs to the finite impulse response filter.

Figure 4:
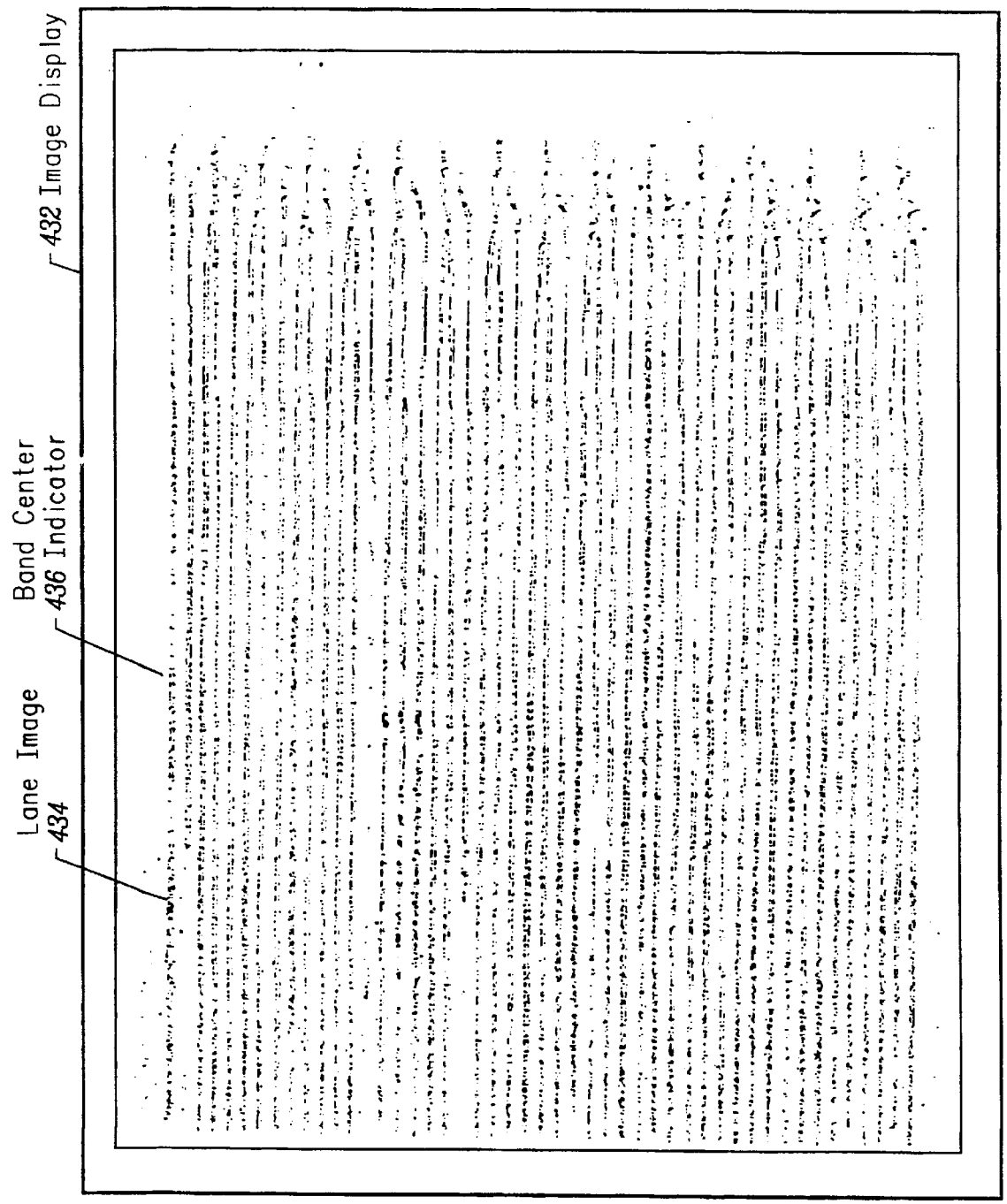
FIG. 4 illustrates example output where the center of the bands have been identified.

At block 370, the output of the finite impulse response filter is an image of the same size as the digital image data 118. This new image includes intensity values of where the back propagation process has determined that band centers exist. The intensity value of these pixels indicate the confidence level that a center of a band exists at a given locationFIG. 4 illustrates the output of a back propagation process that has been trained to identify the center of bands. FIG. 4 includes the image display 432 similar to that of FIG. 1. In FIG. 4, the images have been rotated 90 degrees counterclockwise. The image display 432 includes a lane image 434 that corresponds to the lane image 134. The band center indicator 436 corresponds to a pixel in the image display 432. The pixel's intensity corresponds to the likelihood of a band center existing at the band center indicator 436 location.

Note, in some embodiments of the system, the training data is not updated. That is, the neural net is permanently programmed with the training information. However, in other embodiments, users can replace the training information or add to the training information. This allows some embodiments to compensate for idiosyncratic aspects of particular machines.

The following sections describe the second phase of the lane tracking process where the centers of the bands are connected. The input to this phase are the peak point coordinates and confidence values generated by the point identification phase. The second phase tracks the lanes in the digital image data 118 using a multi-stage process where splines are fit to lanes.

g. Connecting the Dots

As explained previously, the phase in which the splines are tracked to the points, produced by the point identification phase, is named "connect the dots". The dots refer to the points and hence the band centers. In some embodiments, the connect the dots, phase models lanes specifically with Catmull splines. The modeled lanes track the lanes 104 in the gel. The model lanes are also referred to as the splines or tracked lanes.

As with all splines, Catmull splines are defined with respect to tie points (also referred to as control points). The tie points for Catmull splines are evenly spaced. A spline segment of a Catmull spline is defined by the four consecutive tie points that are closest to the points of the segment. That is, a set of four consecutive tie points necessarily imply three spaces between the four tie points, and, by the definition of the Catmull spline, the four tie points then specifically define a spline segment for the middle space.

Each model lane is defined by a set of Catmull spline points where each distinct consecutive group of four tie points, as explained above, define another one of that Catmull spline's segments. All the model lanes have their tie points at the same scan location. The lane tracking program 124 manipulates the splines' tie points in the channel axis to move the splines.

h. Example Method of Lane Initialization

Figure 5:
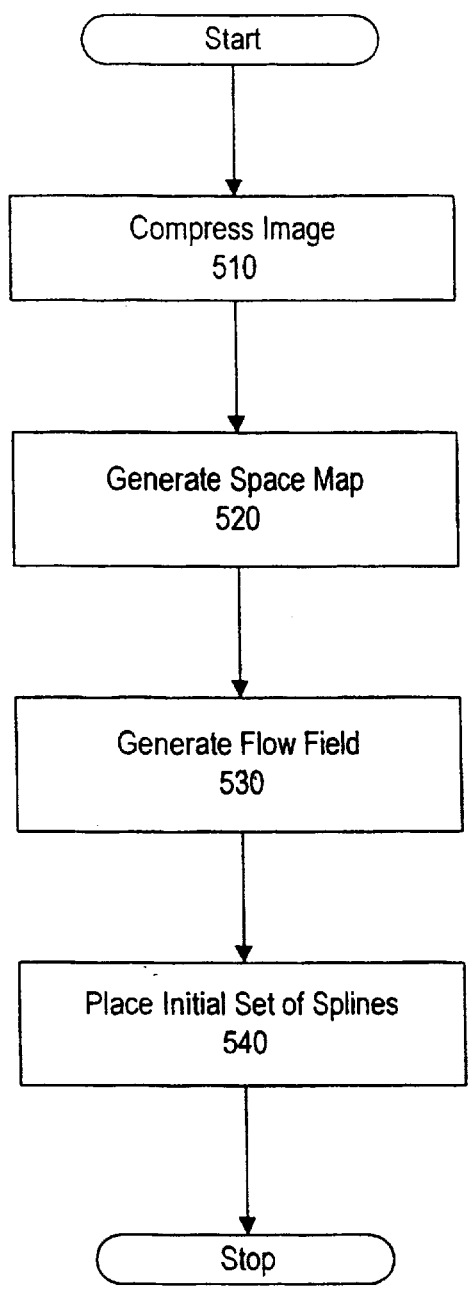
FIG. 5 illustrates an embodiment of a method of initializing the system.

FIG. 5 illustrates an embodiment of the initialization block 250. This initialization block initializes the system for performing the spline fitting.

i. Compression

At block 510, the digital image data 118 is compressed. The compressed image corresponds to the digital image data 118 being compressed, as described below, along the scan axis. The scan axis is the direction perpendicular to the direction of a scan (i.e. along the direction of channel and so therefore the lanes). The channel (or lane) axis is the axis corresponding to the direction perpendicular to the flow of the lanes 104. The compression process is important because the digital image data 118 can be very large. The output of block 510 is an image with only 60 to 90 scans as compared to the original 3000 to 14000 scans. Compression is obtained by setting each pixel in the compressed image to the maximum value across a large number of scans within one channel. This takes advantage of the excess resolution that is inherent in the point image and also the fact that even at the compressed resolution the slope of the lanes is still small. The compression yields much smaller and denser images suitable for standard image processing operations (e.g. small convolutions which is used to compute the flow fields) while simultaneously reducing the time and memory requirements on the computer. This process is describe in greater detail below.

The compression is performed differently depending on the type of process in which the gel 100 is being used. For sequencing images, portions of the image are compressed at dynamically ascertained compression ratios such that the lanes in the resulting image do not exceed a given maximum slope between band centers. For gene scanning, the digital image data 118 is compressed with respect to predetermined compression ratios for different portions of the image as determined by a priori knowledge. The dynamically compressed image is often 200 times smaller than the original digital image data 118, while at the same time having lanes of mild slopes. Also the peak density is greatly increased. The non-dynamically compressed image will typically be 100 times smaller than the digital image data 118. This increased peak density greatly enhances the efficacy and speed of the lane tracking program 124 by using much less memory in the computer 120.

The dynamically compressed image is compressed significantly everywhere in the digital image data 118 except in the areas corresponding to the bottom of the gel 100. This bottom area corresponds to the "primer peaks." The primer peaks correspond to the very short copies of the sample material.

As noted above, for gene scanning predetermined compression ratios are used. In some embodiments, the gene scanning has an approximate compression ratio of 100:1. For the first 400 scan lines (near the primer peaks), a compression ratio of 20:1 is used. For the next 400 scan lines, a compression ratio of 50:1 is used. For the rest of the scan lines, a compression ratio of 130:1 is used. If an gene scan image has 5000 scan lines, then the compressed image would have approximately 61 compressed columns (a 82:1 compression ratio).

The following describes the dynamic compression technique.

A two stage minimal compression is performed to determine how much compression can be done to the digital image data 118. First, the scan axis portion of the point coordinates are compressed by a factor of ten and truncated to integer pixel coordinates. The corresponding binary image is vertically (i.e. in the direction of a scan) thinned so that further compression will not merge lanes. The points from this image are then compressed again but by a factor of four. This provides a total compression of forty.

For each 12.5 scan long segment (patch) of the 40x compressed image (a segment extends across all lanes), the maximum slope for any lane fragment in that segment is determined.

Determining the slope includes the following steps.

First, create a segment image by extracting the sub image of the whole 40x compressed image which corresponds to the current 12.5 (compressed) scan segment. This new segment includes a few scans of padding for computational purposes.

Next, the segment image is labeled. Labeling involves a combination of closing and thinning operations to join very close, but disjoint lane segments, together. Also this involves making sure that the lanes are no more than one pixel thick. Each segment of the image can then easily be identified as a separate entity using a simplified variant of a standard binary image labeling algorithm. This simplified labeling algorithm would not generally be adequate for general labeling, but because the image has been processed to contain simple one pixel thick lines, without bifurcations, it is adequate for the purposes herein.

A labeled image is created by assigning to each lane pixel a value that indicates the following. First, whether or not the pixel is the first one for its lane fragment in the segment. And secondly, where the next pixel on the lane fragment, if any, can be found. Each lane fragment in the resulting labeled segment is traversed to yield its slope, which is computed just using endpoint coordinates.

The maximum lane slope is obtained by only considering lane fragments over 6 scans long and then taking the ninety-fifth percentile of the slopes of the remaining lane fragments. Very short fragments are not considered because they are inherently untrustworthy. The ninety-fifth percentile slope, versus the maximum slope, is used to avoid possible aberrations.

Thus, the maximum slope has been determined.

Next, for each of the segments, the lane tracking program 124 computes the maximum allowed compression. This is done by computing the factor difference of the current slope with respect to the forty times factor compressing versus the given maximum allowed slope. This factor is then multiplied by forty to yield the maximum allowed compression for the segment. For example, assume the maximum allowable slope is one, and a segment has an associated slope of 0.1. Since the original compression is forty, and the maximum allowed slope is ten times greater than the forty compressed slope, then the computed allowed compression would be forty times ten equaling 400.

Finally, at the end of block 510, the following is performed. For each of the segments in the original image, the lane tracking program 124 computes the compressed coordinates of the pixels. This is done by dividing the coordinates by a pixel's corresponding segments compression factor and then truncating. The compressed image is formed by creating the binary image which corresponds to the compressed coordinates.

Figure 6:
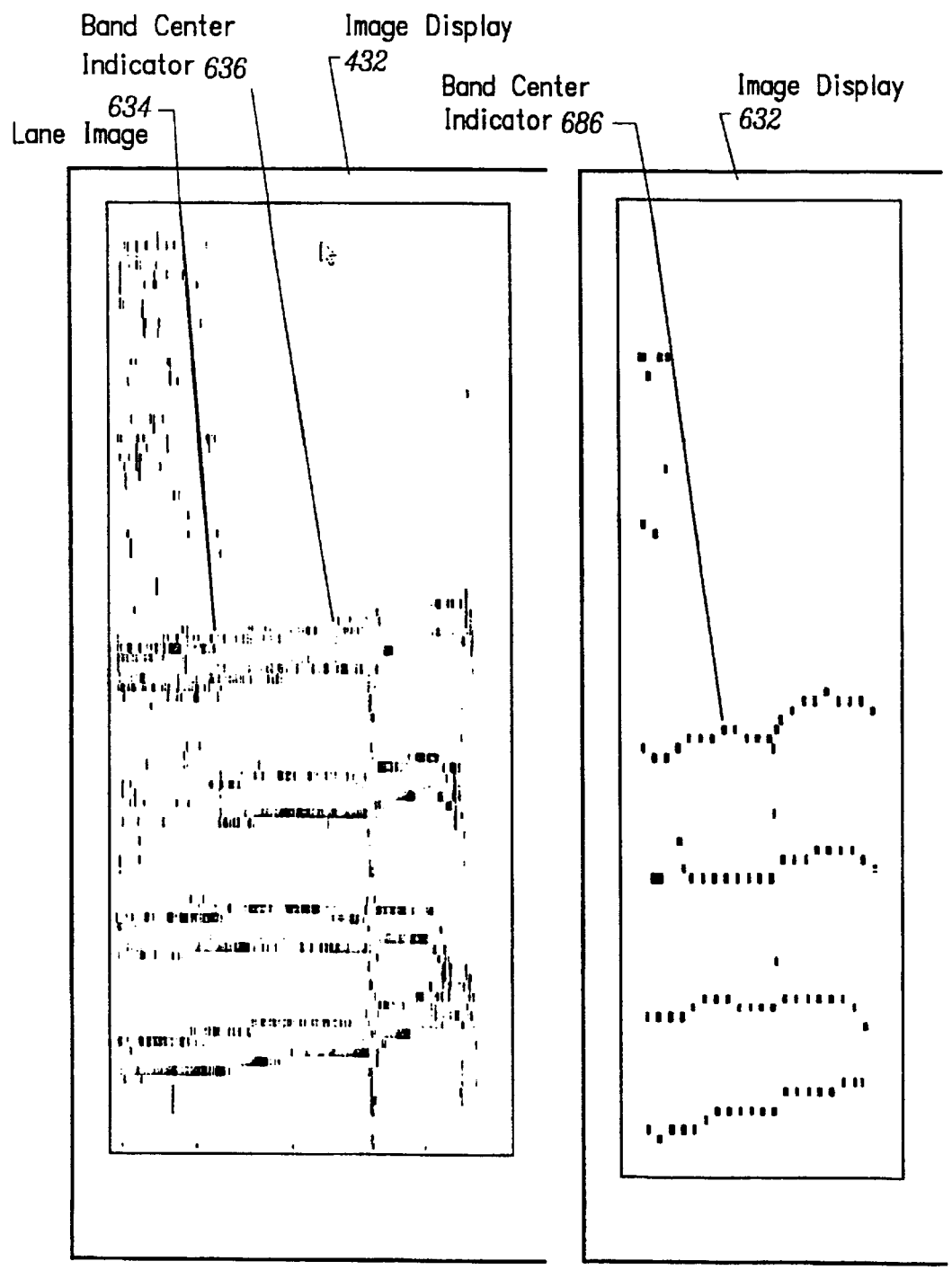
FIG. 6 illustrates example output during part of the initial estimate.

FIG. 6 illustrates the example output of the compression block 510. A band center indicator 686 corresponds to a portion of the lane image 634 having the band center indicator 636. The image display 432 illustrates the output of the point identification process. The image display 632 illustrates the output of the compression process.

ii. Space Map Generation

At block 520, a space map is generated. The space map indicates the distance between adjacent lanes anywhere in the image. These adjacent lanes are actually virtually adjacent lanes because the space map indicates where possible lanes could exist, and not where lanes actually do exist. The space map therefore provides the lane tracking program with a general idea of how far lanes are spaced from neighboring lanes, for any area of the image.

The following describes the process of generating a space map. First the compressed image is vertically thinned. After the image is compressed, the image typically includes a small vertical line of pixels (i.e. within one scan) representing a peak point. The center of the small vertical line is a good estimate of the center of the corresponding bands in the original scans that map to the vertical line's compressed scan. The vertical thinning replaces the block of pixels with one central pixel.

Next a difference image is then created by determining the distance from each peak to the next peak across lanes within each scan. From the difference image, one number is computer as the nominal value for lane spacing for the entire image. This is done using the following technique. The first significant peak, i.e. the first mode, within a histogram of reasonable values in the difference image is found. The peaks in the image are found by analyzing the first and second derivatives of the histogram. The algorithm is made noise resistant by employing Derivative of Gaussian and Laplacian of Gaussian filters to determine the first and second derivatives respectively.

Next regions of the difference image are then analyzed to determine each regions specific spacing. The confidence of each regions spacing is also computed. The confidence is positive only if the difference image indicates that the spacing for a region of the image is close to the global nominal value or twice the global nominal value. The number of points in the region is also a factor in each confidence value. The confidences and the spacing values, as a whole, correspond to the confidence map and spacing map respectively.

The spacing map and the confidence map are used to complete the spacing map to the extent possible using an iterative growing process. The following describes an example of an iterative growing process. The space map is populated with the values corresponding to only the high confidence values of the input space map. Pixels that border on the edge of these pixels are analyzed to see if they have spacing values that are consistent with their neighbors with high confidence. If these bordering pixels have such spacing values, these pixels are set in the space map to their corresponding values. This process iterates until no new consistent pixels are found.

The iterative growing process may not complete the space map. If this is the case, then there are areas of the space map where there was not enough information to deduce a local spacing from the image. These holes are filled by interpolating between computed space values. This can be done as a three stage process; each stage being a one dimensional interpolation. The first stage interpolates along one axis. The second stage interpolates along the first stage result with another axis. The third stage interpolates the second stage result along with the first axis.

There can be additional unfilled areas of the space map (e.g., along the edges of the filled areas). These areas are filled by extrapolation. First, the space map is extrapolated in one direction, and then the result is extrapolated in the other direction. In one embodiment, extrapolation is performed by copying the edge values along the axis of extrapolation.

Finally, the space map is interpolated, or stretched back, to the image size.

iii. Center Initialization

Next, a subphase of the initialization process, involves a center initialization of the lane tracking program 124. The center initialization accomplishes two goals. The first goal is to find the lanes 104 to be tracked. The second goal is to track those lanes 104, but just for the center of the digital image data 118. The lanes 104 tend to be straight in the central portion of the gel 100, but curve towards the ends. The center initialization uses this information to identify where the lanes 104 are and perform a first approximate fit to those lanes.

Generally, the center initialization phase uses the space map to create a model lane (spline) for each possible lane in the digital image data 118. Note that even areas that do not indicate any peaks can have model lanes whose position is determined with respect to the existing peaks and the space map.

The center initialization phase then uses multiple invocations of the local optimization process. This local optimization helps track the lanes in the center of the image. The local optimization tracks the lanes to fit the peaks, the space map, and a number of regularization constraints. The output of multiple local optimization invocations is then analyzed to determine which of the model lanes do not seem to correspond to any points. These "phantom lanes" are then removed from further consideration. The resulting lanes seem to then correspond to the lanes that were generated from sample wells 102 containing sample material.

Center initialization will now be described in greater detail. Center initialization is a boot strapping process. The first step is to determine the densest scan, that is, the scan with the most peaks in the center portion of the thinned, compressed image. At this point, it is assumed that there is a loaded lane at each peak in the scan. Remember that one pixel in the thinned, compressed image can correspond to between 30 and 200 pixels of the original image. Therefore, this boot strapping process typically finds most of the lanes.

iv. Flow Map

One of the first steps in center initialization is to generate the flow map or flow field. The lane tracking program 124 extrapolates the initial model lanes for the rest of the scans in the center portion of the image using the flow map. The flow field is generated at block 530. A flow field is a map or image of the expected trajectory of a track occurring at any point in the compressed image.

The following describes how a flow field is computed. At each pixel in the image, the lane tracking program 124 finds the directional filter which gives the maximum response at that pixel. That maximum response value and direction is encoded as a complex number in the initial flow field map. This substep is now described in greater detail.

The directional filters are oblong Gaussians whose principle axis is that filter's direction (or orientation). Filtering the image with a directional filter yields an image whose pixels correspond to the amount to which the input image "is going in the direction" of that particular filter. Filtering the input image with respect to a range of orientations, at discrete increments, yields a sequence of images which are the response of each pixel to every one of the orientations. A maximum image can be formed by, for each pixel, finding the image in the oriented sequence of images whose value for that position pixel is the maximum. For each pixel, that maximum value, in conjunction with the orientation of the sequence image from which it came, can be encoded as a complex number in the initial flow field map. This can be performed using the following steps: First, filter the input image for the next orientation. Then, compute the next maximum image result as the element wise maximum of the new result image with the accumulated maximum result image of all previously computed filters.

To increase the robustness of the process, the image is then smoothed, by convolving with a kernel of one's, and compressed. The compression is done by taking a maximum value along each axis for some range of pixels. The image is then expanded back to its original size bilinear interpolation to yield the final flow yield map.

Next, at block 540, an initial set of splines are placed. These splines are then provided to the local optimization process, as described below. Note that these initial splines do not contain any anchor lanes. The local optimization is typically much more effective if it is seeded with anchor lanes. However, for this initial set of curves, the local optimization process is modified to start with no anchor lanes. An anchor lane is a model lane that is assumed to be a properly placed model lane (a good fitting spline). Anchor lanes are explicitly prevented from moving during local optimization computations. Movements of other lanes are relative to anchor lanes. Block 540 is described in greater detail below.

At block 550, an iterative local optimization process is performed on the initial set of splines to anchor all good fitting splines. Block 550 is performed as follows.

Splines are analyzed to see which ones seem to be fitting well with the points that are close to them. "Good fitting splines" are then grouped into blocks of continuous good fitting splines. The blocks of good fitting splines can include trapped phantom splines. Phantom splines are model lanes implied by the space map but that do not exist. The largest of these contiguous blocks of good fitting splines is used as the anchors to the next local optimization. The local optimization is then executed with its only given splines being the anchor splines. The remaining splines are initialized by the local optimization process by extrapolating from the anchor splines using the space map.

The splines output by the local optimization are again analyzed to find good fitting splines. These good fitting splines are merged with the good fitting splines output from the first optimization. Any duplicates are removed. The merged set of good fitting splines is then analyzed to find the largest new contiguous set of good fitting splines. These contiguous sets of good fitting splines are then used as the input to the next local optimization step. These steps then iterate until all of the splines are part of the anchor splines.

Finally, the local optimization is executed again such that non-contiguous anchor splines are provided to the local optimization process.

At block 560, any splines that are not fitting well to points in the image are removed. That is, any splines that are not the closest spline to any point are removed. The result of block 510 through block 560 is a set of splines that are associated with corresponding image lanes.

i. Example Method of Local Optimization

Figure 7:
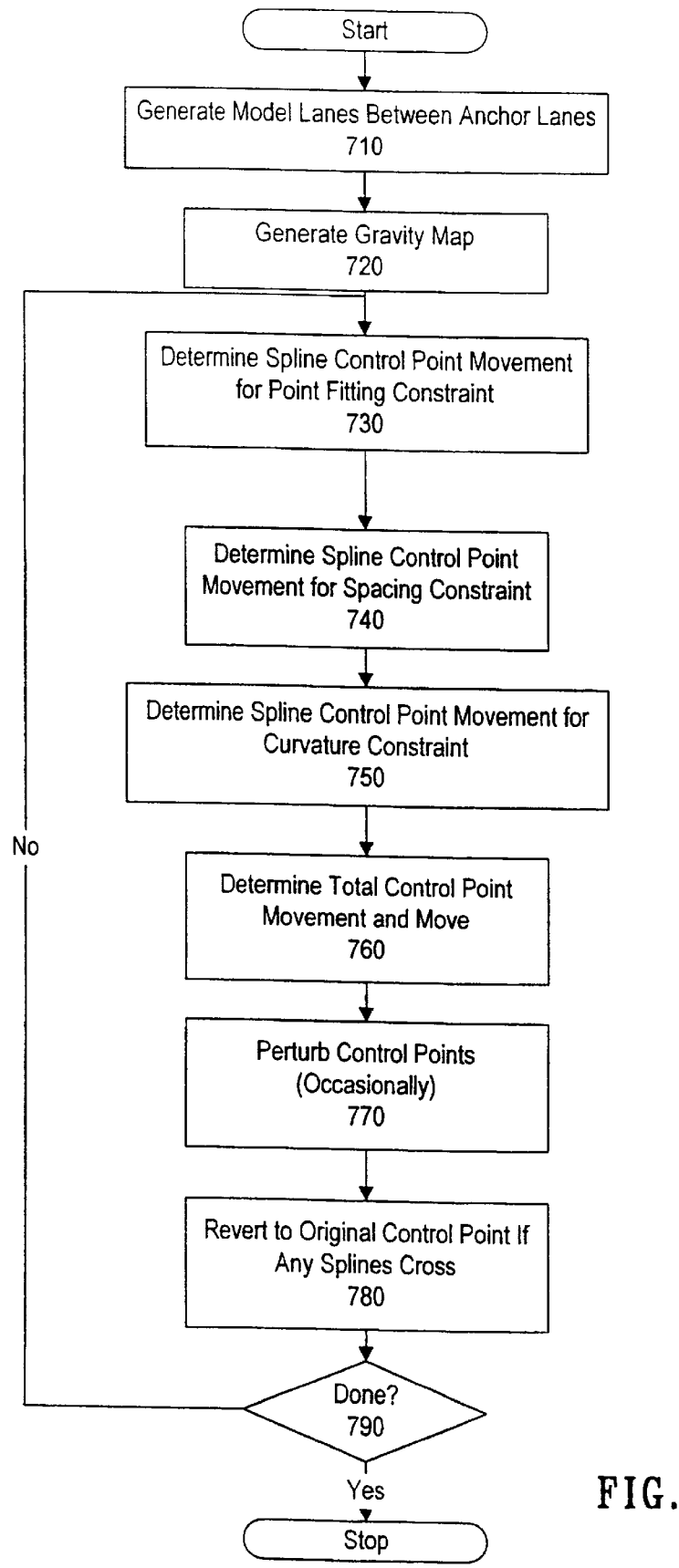
FIG. 7 illustrates an embodiment of a method of performing a local optimization of the fit of a set of splines to lane images.

FIG. 7 illustrates an embodiment of a method of performing a local optimization of the fit of a set of splines to lane images. Local optimization performs an initial fit of the splines to the lanes 104. The problem with global optimization is that it works very well but it is compute intensive. Local optimization does not require as much processing as global optimization, but provides a good starting point for global optimization.

In local optimization, the lane tracking program 124 has each spline controlling its own action. Generally, the splines try to move themselves so that the spacing remains about the same between lanes. The splines try to move so that the spline is over the data points that correspond to band centers, and not be between two data points. The splines also try to move so that they follow the flow map. The following describes the local optimization process in greater detail, and in particular, with descriptions of the cell automata process.

In general, the cell automata is an iterative self organizing algorithm for arranging spline tie points such that the corresponding splines tend to converge to a stable pattern as dictated by structural as well as regularization constraints. For the lane tracking program 124, the structural constraints include the peak points (as contained in the compressed image) and the space map. The regularization constraints include the minimization of lane curvature and the difference between the shape of consecutive lanes. At each iteration, an aggregate value is determined for each tie spline. The aggregate value corresponds to where the tie point should move in order to satisfy all the constraints as given by each constraint's movement value. Since these constraints are, in general, not all perfectly simultaneously satisfiable, the final aggregate movement value will not solve the constraints. However, moving each tie point a small fraction of the aggregate movement value will in general tend to produce a system whose next movements are smaller (in some total magnitude sense). Through repeated application of this process, the process tends to converge to a system which no longer improves over some arbitrarily large number of iterations.

In the lane tracking program 124, the tie points are Catmull tie points and so are, by definition, evenly spaced. This makes the computations more efficient but it is not required. Furthermore, the tie points' movements are restricted to the channel axis. This greatly simplifies the algorithm but is also not required.

The following paragraphs now describe the embodiment of FIG. 7 in detail. The cell automata has, as its input, some number of anchor lanes, and the compressed image. The output is a larger set of anchor lanes.

At block 710, the lane tracking program 124 generates an initial set of model lanes between the anchor lanes. This is done by creating a "full tooth comb model" around the anchor lanes. A full tooth comb model corresponds to having every lane loaded, between the anchor lanes, in the gel 100.

The first step in block 710 is to calculate the "(model) lane distance," using the space map, between the anchor lanes. The lane distance is an estimation of how many lanes away one given lane is from the next given lane assuming a full tooth comb model. For example, if lanes between these anchor lanes were not loaded with samples, then a corresponding lane distance of two or greater would be expected indicating at least one "phantom" (i.e. unloaded) lane between those two anchor lanes. The distance is taken with respect to the center scan.

Next, the lane tracking program 124 creates model lanes for the phantom lanes between any two anchor lanes, as necessary, by linear interpolation.

Next, the lane tracking program 123 creates additional model lanes for potential lanes, phantom or otherwise, by extrapolation. These additional model lanes come before and after the anchor lanes, as necessary. The new lanes are just shifted replicas of the closest anchor lanes. Model lanes are added until they bound all the peaks in the compressed image.

At block 720, a gravity map is created. The gravity map gives the base movement, with respect to a scan, to move the spline toward any peaks (centers of bands).

The gravity map is formed by convolving the compressed image with an edge detector kernel. Specifically, the kernel is a one dimensional gaussian filter. The filter is applied along the channel axis. Half of the gaussian filter has been negated and the center value is 0. The result is a gravity map with negative values on the positive side of a peak and vice versa. These movement values draw splines on either side of the peak toward the peak.

Block 730 through block 790 are now repeated until enough local optimization has been performed.

The line tracking program 124 determines the base spline tie point movement from the gravity map. The base spline tie point movement includes block 730 through block 750, and a portion of block 760.

At block 730, the line tracking program 124 determines the portion of the movement due to the point fitting constraint. This is now described in detail. First, a spline map is generated. This spline map includes the model lane's position at each scan. Next, the lane tracking program 124 generates point fit movement values. This point fit movement value is determined for each tie point by taking a weighted sum of the gravity movements for each scan on the tie point's lane that is between the previous and the next tie point. The weights are given by a gaussian function. The gaussian function has a standard deviation that is half the distance to the next tie point, is centered on the tie point, and whose extent is from the previous to the next tie point on the model lane. In this way, point fit movements, on a certain scan, effect both of the tie points that bound the scan.

Next, at block 740, the lane tracking program 124 determines the part of the movement due to the spacing constraint. This is now described. The lane tracking program 123 first determines the discrepancy between the expected distances between the model lanes, as given by the space map, and the actual distances. The tie point matrix (versus some analytic form or finer sampling of the splines, which are used in other embodiments) is used to determine this discrepancy. The actual distances are computed by taking the simple difference between the channel coordinate of a tie point with the one above it. This yields a difference matrix with one less row then the tie point matrix because of there are N-1 spaces between N lanes). The space map distances are computed by indexing into the space map for each tie point in the first N-1 lanes. This matrix is therefore the same size as the actual difference matrix. Subtracting one from the other gives a spacing discrepancy matrix. Taking into account the inaccuracy inherent in the space map, the magnitude of the each space movement in the discrepancy matrix is decreased by 1. Therefore, a discrepancy less than or equal to 1 is taken to be no discrepancy at all.

Once the spacing discrepancy matrix is computed it is necessary to translate it into a base spacing constraint movement for the tie points. Each spacing discrepancy element corresponds to a pair of tie points on adjacent lanes, one directly above the other. The determination of which tie point to move, the top or bottom one, to reduce the discrepancy is a depends upon various factors and contexts. If the cell automata is invoked with no given anchor lanes (no fixed lanes) then the choice changes every 20 iterations. If the cell automata is called with anchor lanes then the top tie points will be moved for the lanes above the anchor lanes, the bottom tie points will be moved for the lanes below the bottom anchor lane, and for any lanes between anchor lanes the choice will alternate every 20 iterations.

Next, at block 750, the lane tracking program 124 determines the part of movement with respect to the curvature constraint. This is done as follows. First, the lane tracking program 124 determines the ideal regularized trajectories by computing the position of a tie point on a lane as the average of itself and that tie point's two neighbors. Again, this is done using the tie point matrix in some embodiments, while in other embodiments, analytic form or finer sampling of the splines is used. Next, the lane tracking program 124 determines the curvature constraint movement by subtracting the current positions from the ideal regularized trajectory.

The movements due to the regularization and space map constraints are now adjusted to give less importance to tie points that are not close to points (peaks). This is accomplished by attenuating a portion of their movement with the normalized movement due to the peak point constraint.

At block 760, the base spline tie movement is determined from a weighted sum of partial movements generated in block 730 through block 750. Additionally, the lane tracking program 124 overrides portions of the movement that correspond to tie points that are extremely close so that the tie points are the movements as given by the space map. Also, in block 760, 0.2 of the total movement is added to generate a new set of tie point coordinates.

At block 770, occasionally, the lane tracking program 124 perturbs the tie point coordinates with some random noise. This helps the lane tracking program 124 in the possible event that it becomes "stuck" in a bad configuration.

At block 780, the original set of tie point coordinates are used if any of the splines cross. Otherwise, the new movement coordinates are used.

At block 790, a test is performed to determine whether enough iterations of block 720 through block 780 have been performed. In some embodiments, during the initialization, 1000 iterations are performed, and 600 iterations are performed otherwise.

After four iterations of the above process, the global optimization is performed.

j. Example Method of Global Optimization

Figure 8:
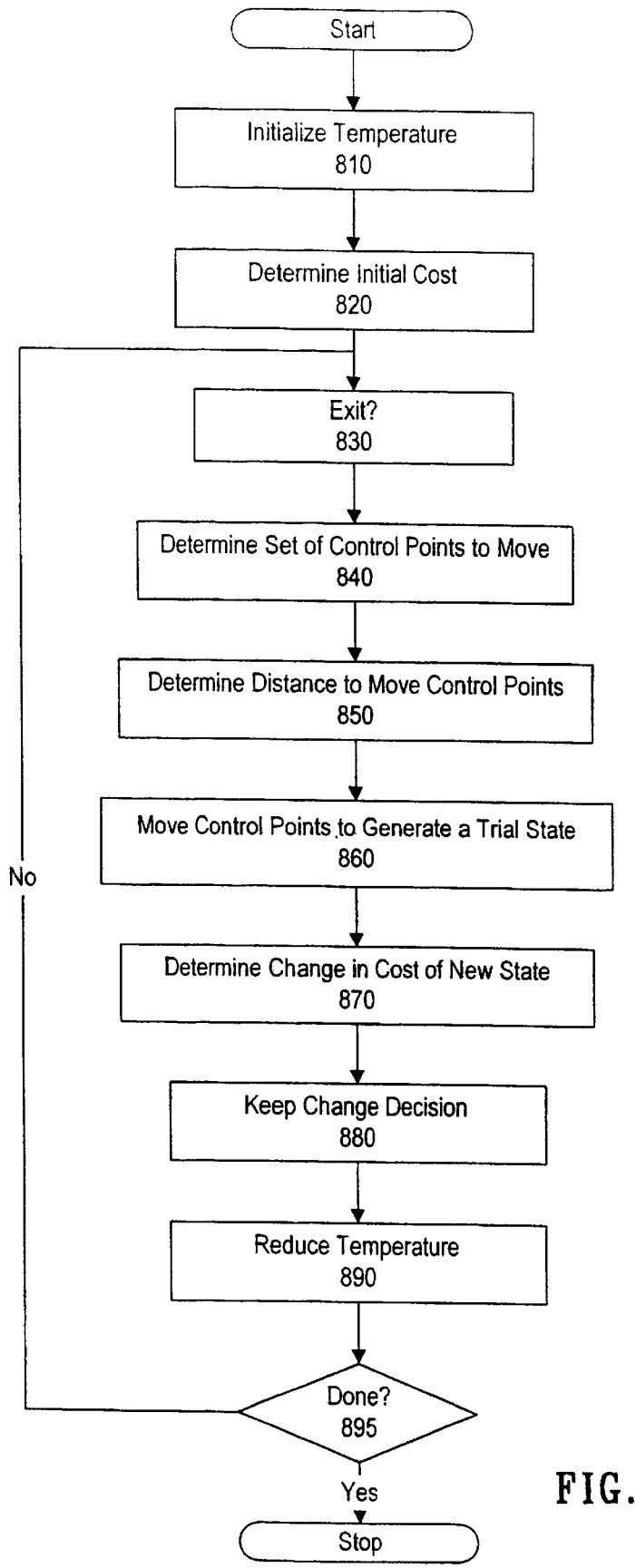
FIG. 8 illustrates an embodiment of a method of performing a global optimization of the fit of a set of splines to lane images.

FIG. 8 illustrates an embodiment of a method of performing a global optimization of the fit of a set of splines to the lane images.

The global optimization process takes as input the set of splines from the cell automata and then fits them to the lane images. Regarding the input set of splines, It is assumed that the set of splines all track existing lane images. The global optimization refines the cell automata fit as well as fitting the areas of the image not previously tracked (for example the tops and bottoms of the lanes).

The global optimization can be thought of as a process of shaking a portion of one or more splines to produce a trial state. The results of the shaken portions of the splines are evaluated by the cost function to determine the goodness of the fit. The goodness of the fit corresponds to whether the splines fit better to the lane images. If the fit is better (i.e. lower energy/lower cost) the global optimization process will always accept the trial state (as in standard simulated annealing). If the fit is worse and the dynamic simulated annealing process indicates a poor fit for the shaken portion of the image then occasionally, as given by the simulated annealing acceptance function, the trial state is accepted anyway.

The global optimization cost is computed as a combination of structural as well as regularization costs. The structural costs include the fit of the model lanes to peak points (as contained in the compressed gel image) and the space map (which contains a derived estimation of the distance the next lane should be from another lane at any given point in the compressed image). The regularization costs include lane curvature, lane similarity and lane slope variance.

The global optimization is based on an algorithm called simulated annealing. Specifically, some embodiments employ a variation of the "Metropolis Algorithm." Simulated annealing is a method for global optimization. Given a system that is defined by a given set of parameters (e.g. model lanes defined by Catmull spline tie points), and a cost (or error) function that measures the error associated with the parameter values, an error surface is defined (over the support of the error function). The error surface may contain many local minima, but there exists a minimum value somewhere on that surface. The point on this error surface with that minimum value is called a global minimum. Most, optimization algorithms perform local minimization. That is, given some initial set of parameters that define some initial error, a local minimization algorithm will always produce a sequence of parameter transitions whose corresponding errors form a monotonically decreasing sequence. It has no ability to obtain the better or global minimum that might be just over a small nearby hill, from its current position on the error surface. (This is because climbing the hill would be a transition to a higher error and so would violate the monotonically decreasing error sequence.). Unlike attempting to find a global minimum, finding the nearest local minimum is a fast and deterministic process. Unfortunately, the error of the local minimum might be much larger then the global minimum. Thus, a global minimum is more desirable.

The basic simulated annealing process is as follows. This description is provided to help identify differences between the basic simulated annealing process and the process used in some embodiments of the invention.

Initialize the state of the system. This corresponds to assigning some starting values to the parameters that are to be optimized.

Initialize a temperature parameter to a relatively high value.

Determine the initial (current) cost (or error) of the system. The cost of the system is given by the cost function. The cost function quantifies the goodness of fit by assigning a number to any possible configuration (state) of the system. The lower the cost the better the fit.

While the temperature is above some value perform the following:

For some number of iterations:

Determine the next trial state of the system. This involves the use of a generating function which adheres to some generation probability function. The generating probability of the next trial state decreases with the distance from the current state and increases with the temperature.

Compute the cost of the trial state.

If the trial cost is less then the current cost, or the trial cost is higher but is accepted by the acceptance probability function, then set the current state to the trial state.

Occasionally, decrease the temperature according to the annealing schedule.

This paragraph provides an overview of the global optimization process. After center initialization, the resulting splines are extended to the whole using simple linear extrapolation. The now full length splines are then input into two passes of the global optimization algorithm. The global optimization uses the modified version of a simulated annealing to move the tie points of the splines. The goal is a properly tracked image with respect to point fitting, the space map and regularization constraints. The results of the first invocation of the global optimization are passed to the second invocation. The second invocations behavior will be different from the first invocation as dictated by a set of controlling parameters. These controlling parameters take into account that, after the first global optimization invocation, the tracking is typically quite good. Also the system analyzes the output of the first global optimization invocation. If the analysis indicates that the tracking seems to be very good, the global optimization will parameterize the second global optimization invocation such that only a minimal refinement is done. On the other hand, if the analysis indicates the tracking seems to be poor, then the global optimization will parameterize the second invocation for large movements of the splines. This gives the lane tracking program 124 a second opportunity to perform a better match. This process is described in greater detail below.

The following paragraphs describe some important differences between the basic simulated annealing process and the process employed by the global optimziation.

The global optimizer dynamically concentrates its efforts on areas of the image which are ascertained to have a poor fit. This is called "dynamic attention." This is accomplished by selecting the tie points to be moved in the creation of the trial states in proportion to the relative local error associated with them (i.e. worse fit). At regular intervals, the lane tracking program 124 checks to see how well the model lanes fit to the points. At a local level this is accomplished by ascertaining which model lane spline segments bound each point (peak) and assigning some measure of error to the tie points that influence those spline segments. The result is an error map for all the tie points of all the model lanes. The system will select which tie point to move in proportion to the relative error of the tie points using a Monte Carlo method.

In addition to the selected tie point, a selected group of its neighboring tie points will move along with the selected tie point to yield the next trial state. This is called "neighbor tension movement". The amount to which the neighboring tie points are moved is a stochastic process which factors in their distance from the selected tie point and the current temperature.

Also, the global optimization uses "dynamic simulated annealing". In dynamic simulated annealing, the global optimization periodically checks to see which tie points are located in regions where the model lanes' fit to the points is poor. Based upon this information, the global optimization only allows acceptance of a higher cost trial state if the corresponding selected tie point is located in a region where the model lanes fit the points poorly. Otherwise, only a lower cost trial state is accepted.

In standard simulated annealing, as described above, it is possible to accept a trial state which has a greater cost (this is how simulated annealing escapes from local minima). However, if some local region of the state seems to be a very good fit, then allowing higher energy jumps will generally produce slower convergence. Also, possibly, although rarely, a jump to a very bad state may be made for which the system may not have enough iterations left to recover from. Therefore, it seems generally beneficial to not allow jumps to higher energy in the case of a very good fit. Note that, theoretically, this can provide less than optimal tracking because there is a limit to how well any function can judge the optimality of the system with respect to a local fit. In general, it may be that a better local configuration yields a worse global optimization. Fortunately, for this application, empirical evidence indicates that a local fit measurement which takes into account a reasonable amount of tie points yields a very effective metric. In other embodiments of the invention, a slower convergence is used.

In the global optimization, a "good lanes rule" also helps increase the speed of the optimization. The good lanes rule is another local metric. Periodically, the global optimization determines which lanes seem to be excellent fits in their entirety and checks to see if there are lanes which seem to have a very bad fit close to the excellently fitting lanes. The good lanes rule modifies the shape of those bad lanes to be more like that of the closest good lanes. This good lanes rule is effective at moving the system out of bad configurations that are wide spread.

The good lanes rule is now described in greater detail. The usual global optimization's method of changing the system configuration is to select a tie point and to move it and some number of its neighbors some amount. Sometimes, the system, usually at initialization, is in such a bad state that moving a few tie points with respect to some annealing schedule will not improve the state sufficiently. This can occur, for instance, when many contiguous lanes are tracking incorrectly but are self similar. Moving a local area of tie points in such an area disturbs the regularity constraints and so yields an increase in cost so large that this movement would never accepted.

If a very bad lane is between two very good lanes, then the shape of the new lane is a weighted average of the three lanes. The weighting takes into account the goodness of fit metric of the three lanes and the distances of the two good lanes to the bad lane. If a very bad lane is within a reasonable distance of just one very good lane, then the weighting takes into account the goodness of fit metric of the two lanes and the distance between the two lanes.

As stated above, the system checks for an application of the good lanes rule at a periodic basis. However, when a lane has been reshaped by the good lanes rule it is prohibited from having the good lanes rule applied to it for another two periods.

The details of the global optimization will be described in relation to FIG. 8.

At block 810, the initial temperature is set.

At block 820, the state of the system is initialized. This includes determining an initial cost of the system and setting the values of the initial parameters. The cost function is described below.

Block 830 through block 895 are now repeated twice, with thirty-five batches per repetition.

At block 830, for every five batches, a test is made to determine whether the fit is sufficient so that no more batches are needed.

At block 840, a set of control points to move is determined. This is done by first, at every specified number of batches, use a local estimation of error to set a flag for each tie point to one if its error is large enough to suggest that it would benefit from the ability to take jumps to higher cost and zero otherwise. At every specified number of batches, use the good lanes rule to change ill fitting lanes to be like neighboring good lanes (if any). At every specified number of batches, use a local estimation of error to produce the dynamic simulated annealing data. This uses the Monte Carlo probability data used in the selection of tie points for the trial states. The data will bias the system to select tie points in areas of the image with higher error.

For the number of iterations per batch being equal to the number of tie points, block 850 through block 880 is repeated.

The lane tracking program 124 selects the tie point to be moved Perhaps some neighbors will also be selected, as dictated by the dynamic simulated annealing Monte Carlo data.

At block 850, the distance to move the selected tie point(s) is determined. The lane tracking program 124 uses the Cauchy generating function to compute the directed distance to move the selected tie point. The lane tracking program 124 also selects the neighborhood "radius" of tie points around the selected tie point to move. The neighborhood is between zero and two, inclusive. The word radius means that the neighborhood of tie points around the selected tie point to be moved are those that are within the radius number of lanes and the radius number of tie points along the lane. This is a 2-d spatial neighborhood. Once the neighbors are selected, the distance to move them is also computed.

At block 860, the selected tie point(s) are moved to generate a new trial state.

At block 870, the change in cost for the trial state is determined. Note that this change in cost is efficiently computed by only determining the cost with respect to the tie points whose positions have been altered for the trial state. The calculation of the cost is now described. The lane tracking program performs the following steps.

Calculate Calculate each point cost with respect to the point's two bounding model lanes. The calculation is the undirected distance from the point to one of the lanes times the undirected distance from the point to the other lane. This number is then normalized to a standard lane spacing of ten. The unnormalized calculation is actually the combined "probability of lane ownership" weighting of the distance between each of the lanes to the point. The "probability of lane ownership" is given by the ratio of the distance of a point to a lane to the distance between the two lanes. A special calculation is done for edge points that are before the first lane or after the last lane. The bounding model lanes cost is the sum of the point errors prorated to the number of tie points (versus the number of peak points). This prorating is done so that the difference between the number of peak points versus the number of tie points does not change the relative importance of point cost to the other costs from image to image(which are all relative to the number of tie points).

Calculate the spacing cost. This is done using the tie point matrix (versus some analytic form or finer sampling of the splines, which are used in other embodiments). The base spacing cost matrix is obtained by subtracting the current spacing from the spacing expected by the space map. Since, unlike the cell automata, the space map is the spacing with respect to all the lanes, loaded or not, and the global optimization only has the model lanes for the found loaded lanes. The global optimization "walks" the space map from one global optimization model lane to the next, inferring the phantom (unloaded) lanes and accumulating the expected spacing between model lanes. The spacing cost matrix is attenuated using a nominal tolerance of 15%. That value increases toward the outer lanes and toward the primer peaks. A spacing error beneath the tolerance is set to zero. This attenuation reflects the empirical evidence of the specific inaccuracies of the space map. The total spacing cost is the squared sum of the space cost matrix elements.

Calculate the curvature cost. This is done using the tie point matrix (versus some analytic form or finer sampling of the splines, as are used in other embodiments). The base curvature cost matrix is computed as the difference between the slopes of consecutive spline segments. The differences are taken as the simple difference of the position of consecutive tie points within each lane. Since the tie points are aligned in the same evenly space channels for all the lanes, only the channel axis part of the tie point position is used in the difference calculations. The elements of the base curvature cost matrix are attenuated toward the outer lanes and near the primer peaks. The total curvature cost is the squared sum of the curvature cost matrix elements.

Calculate the lane similarity cost. This is done using the tie point matrix (versus some analytic form or finer sampling of the splines, as are used in other embodiments). The base lane similarity cost is computed as the cross lane differences of the simple slopes between consecutive tie points within a lane. The elements of the base lane similarity cost matrix are attenuated near the primer peaks and also for the lane distances between the cross lane slopes. The cross lane slope attenuation just takes into account that if consecutive model lanes are actually multiple lanes from each other, because some lanes between them were not loaded, then they are less obliged to have the same shapes as lanes that are truly consecutive (or close for that matter). The total spacing cost is the squared sum of the lane similarity cost matrix elements.

Calculate the slope variance cost, which favors flat lanes. This is done using just the tie point matrix (versus some analytic form or finer sampling of the splines, as are used in other embodiments). The slope variance vector is computed as the mean of the squared weighted mean centered channel axis coordinates of every lane's tie points. The weighting attenuates the difference from the mean near the primer peak. The total slope variance cost is sum of the slope variance vector.

Calculate the total cost of the trial state as a weighted sum of all the separate costs.

At block 880, a decision to keep the trial state is made. If the cost of the trial state is less then the current state then the trial state is accepted (i.e. it becomes the current state). If the cost of the trail state is greater then the current state and the dynamic simulated annealing process allows higher cost jumps for the selected tie point, then the trial state's acceptance is determined by the (simulated annealing) acceptance function. If the trial state was not accepted, the lane tracking program 124 reverts any changes to the system made to attempt the trial state.

At block 890, the temperature is reduced from the current temperature by the input decay factor (typical value 0.85).

At block 895, if the required number of epochs and batches are performed, then the process is completed.

k. Example User Interface

Figure 9:
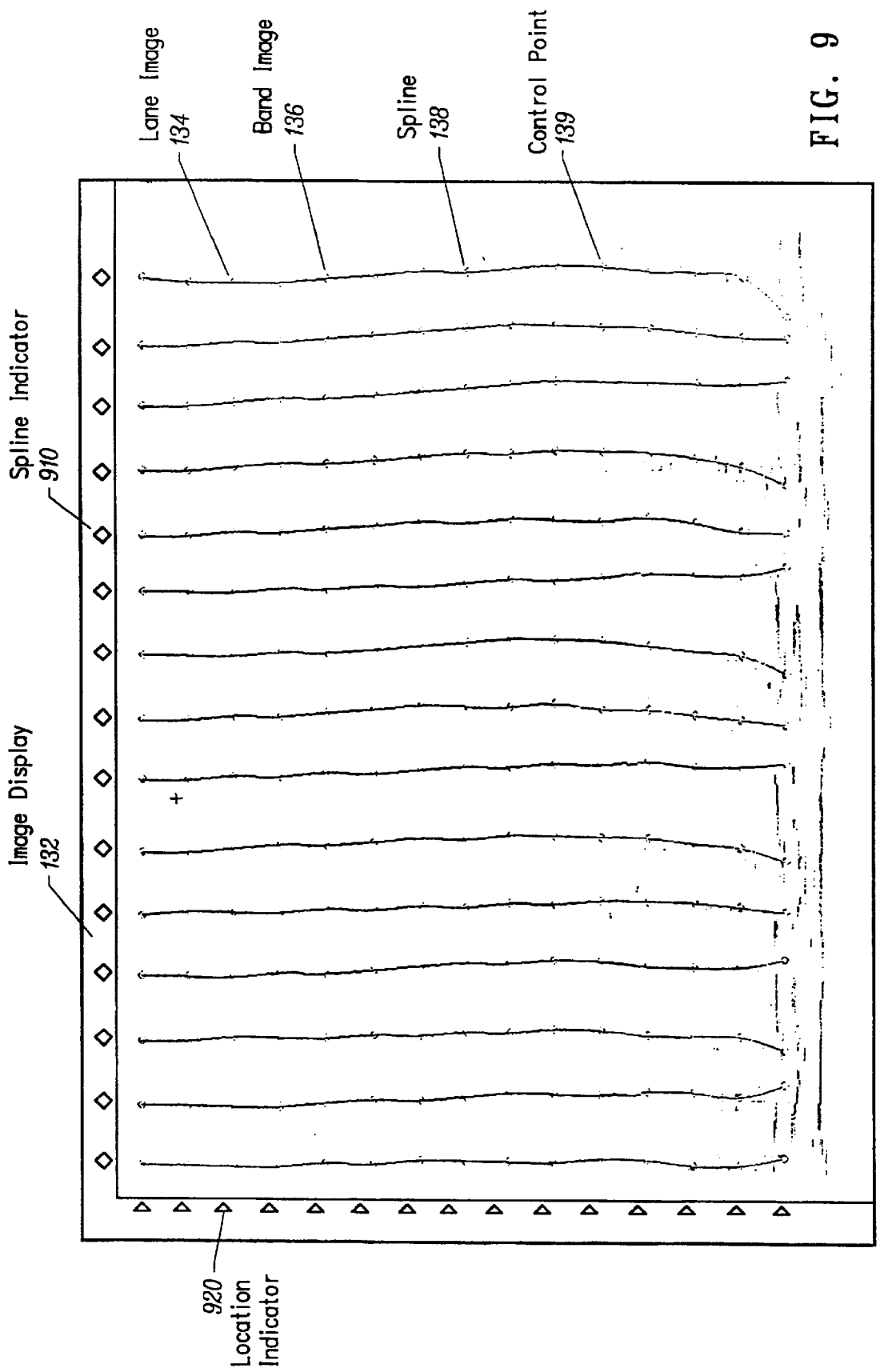
FIG. 9 illustrates a user interface used in the system of FIG. 1.

FIG. 9 illustrates a user interface used in the system of FIG. 1. In FIG. 9, the results of a DNA sequencing process are shown with the lanes being tracked. The image display 132 includes a spline indicator 910 and a location indicator 920. The spline indicator 910 indicates the spline associated with a give lane image. The location indicator 910 the relative location of the bands. The image display 132 allows a user to manipulate a tie point, e.g., the control point 139, to change the tracking of the corresponding spline. However, in some embodiments, a smooth process is used to smooth the shape of the neighboring splines, given the movement directed by the user. In some embodiments, this is performed by performing a global optimization.

Figure 10:
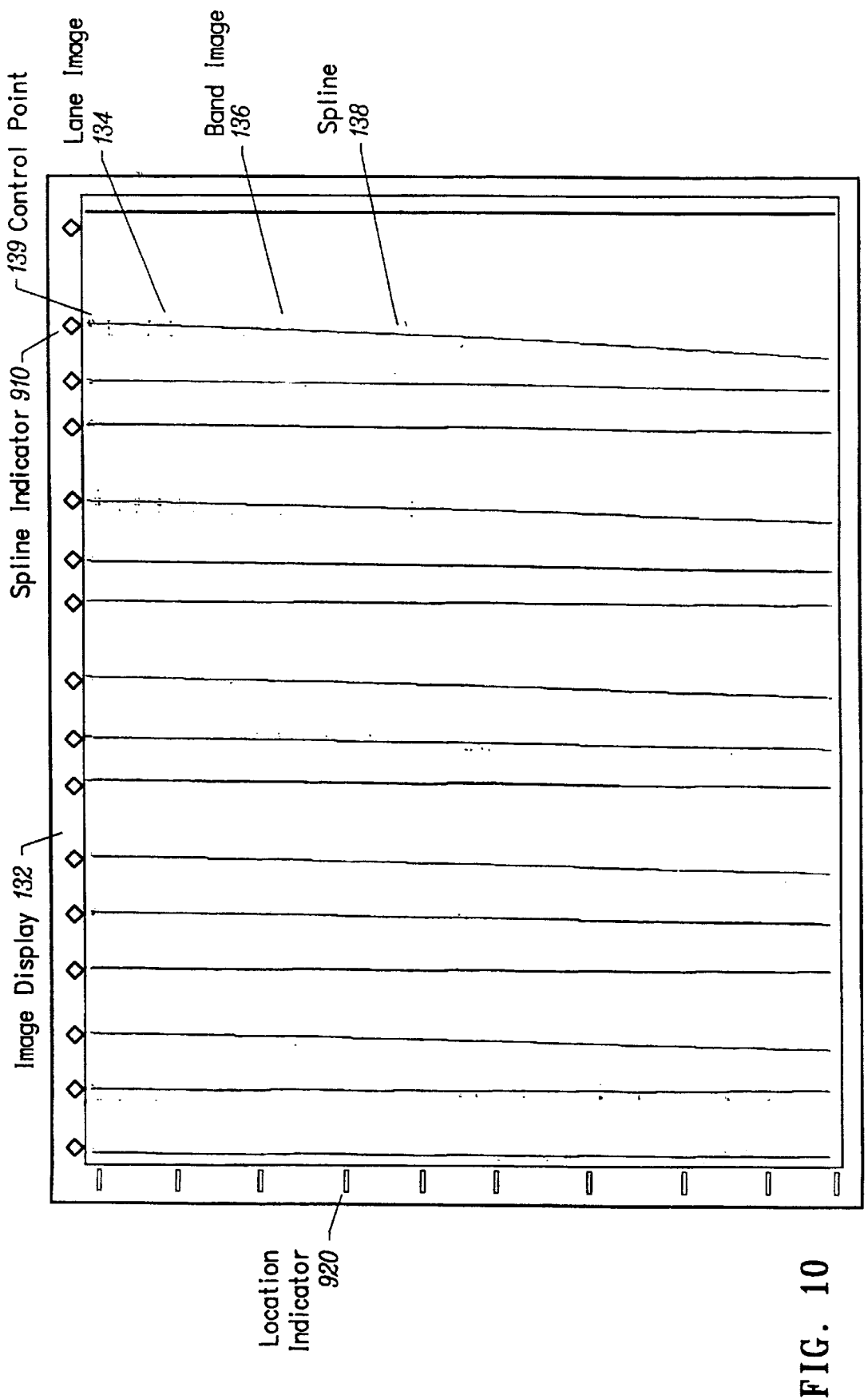
FIG. 10 illustrates a zoomed in view of the DNA sequencing image of FIG. 9.

FIG. 10 illustrates a zoomed in view of the DNA sequencing image of FIG. 9. Note that the specific bands can be seen in this image.

Figure 11:
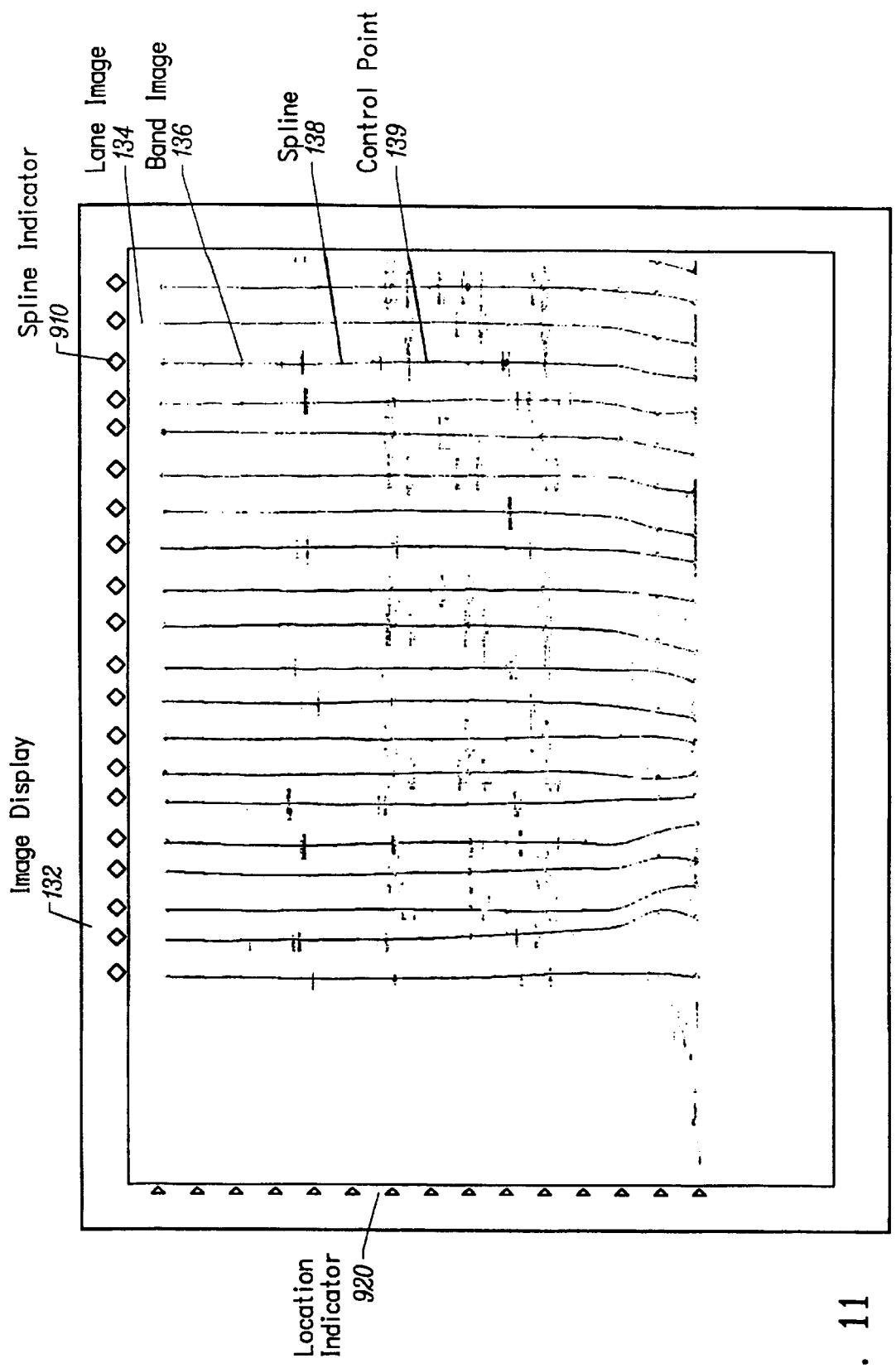
FIG. 11 illustrates the results of tracking the lanes of a gene scanning process.

FIG. 11 illustrates the results of tracking the lanes of a gene scanning process. The bands are spread much further apart than the bands in FIG. 9. This makes lane tracking more difficult. Note that the splines, as fit by the lane tracking program 124, track the center of the lanes.

Figure 12:
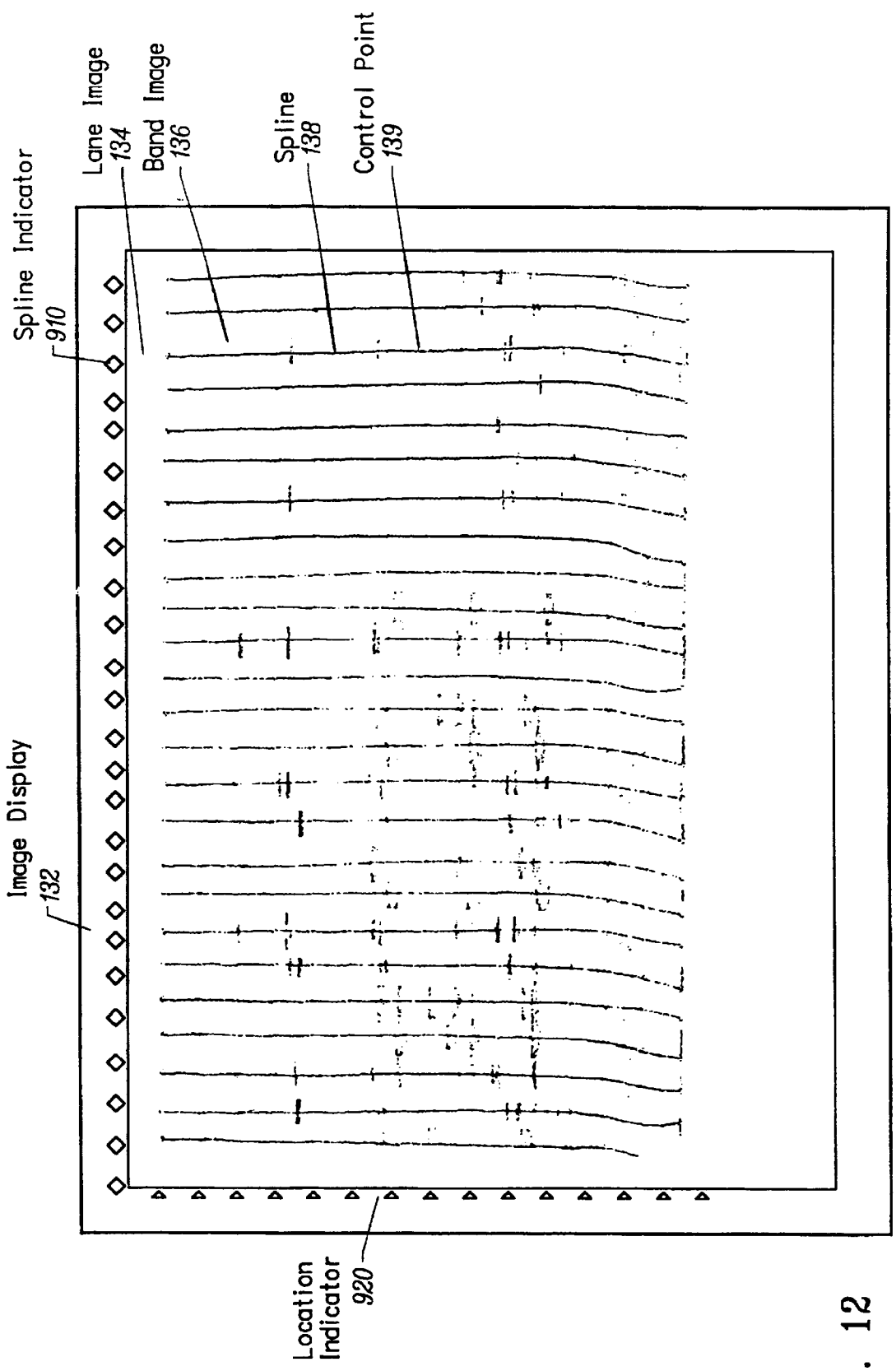
FIG. 12 illustrates a different view of tracking the lanes of the gene scanning process.

FIG. 12 illustrates a different view of tracking the lanes of the gene scanning process.

l. Additional Embodiments

As noted above, many different embodiments of the invention exist. This section describes some additional embodiments.

In some embodiments of the invention, the local optimization is not used except to determine the initial set of splines to use. In these embodiments, the global optimization process is used to fit the splines to the lane images.

In some embodiments of the invention, some of the process steps are performed in parallel or are performed in a different order. For example, in the cell automata, the generation of the component movement values of the base spline tie point movement can be performed in a different order or in parallel.

Additionally, in some embodiments of the invention, where the computer 120 has increased memory and processing capabilities, some steps are not used. For example, some of the compressing steps are not used.

In some embodiments of the system, other processes that create lanes are used. For example, in thin layer chromatography, other gels, plates, and samples are used. Additionally, the type of scanned information can be different. For example, radiation detection can be performed rather than fluorescence. What is important is that this invention can be applied to any lane tracking problem.

In some embodiments of the invention, a special bar code sample is added to the sample wells 102. This causes a section of the lanes to correspond to a particular bar code. This bar code information can also be used in the tracking process as an a priori requirement.

m. Conclusions

A system and method for identifying lanes in images has been described. One example method includes a computer implemented method of determining the locations of lanes of separated samples. Each lane corresponds to a sample being separated by flowing the sample through a media. The method includes the following elements. Place some samples on the media. Cause the samples to separate into the lanes. Create a digital image of the lanes. Fit some curves to the lane images. Each curve corresponds to a lane formed from a separated sample.

This system can be used to track lanes for any of a number of applications. Although specific examples have been provided, many variations of the invention exist. The scope of the invention is defined by the claims and should not be limited to the specific embodiments described herein.

What is claimed is:

1. A method of determining the locations of different lanes of separated samples, each lane of separated samples corresponding to a sample being separated by flowing through a media, the method comprising:

having computer executable logic take a digital image of different lanes, the digital image including different lane images corresponding to the different lanes and fit a set of curves to the different lane images, the set of curves corresponding to the flow paths of the separated samples.

2. The method of claim 1 wherein each lane image in the set of lane images includes a corresponding set of band images, each band in a corresponding set of band images corresponding to a band in a separated sample, and wherein fitting the set of curves includes having computer executable logic create an initial set of curves from the set of band images, wherein the initial set of curves corresponds to the set of curves.

3. The method of claim 2 wherein fitting the set of curves to the set of lane images includes having computer executable logic identify an approximate center for each band image of the set of band images.

4. The method of claim 3 further comprising having computer executable logic compress the digital image prior to identifying the approximate center for each band image, and wherein compressing the digital image includes performing an non-linear compression of the digital image, the non-linear compression being at least partially determined by the slopes of at least some of the lane images of the set of lane images.

5. The method of claim 3 wherein fitting the set of curves further includes having computer executable logic determine a space map from the approximate centers for each band image of the set of band images, the space map indicating an estimated distance between two lane images for a given region of the digital image.

6. The method of claim 2 wherein creating the initial set of curves includes:

having computer executable logic define a first set of curves, the first set of curves being spaced according to the approximate distance between adjacent lane images for corresponding regions of the digital image;

having computer executable logic fit the first set of curves to a central portion of the digital image; and having computer executable logic generate the initial set of curves by removing any curves of the first set of curves that do not sufficiently correspond to a lane image in the central portion of the digital image.

7. The method of claim 1 wherein the set of curves includes a first curve and the different lane images includes a first lane image, the first curve having been identified as having to be fit to the first lane image, and wherein fitting the set of curves includes having computer executable logic perform a local optimization to fit the first curve to the first lane image.

8. The method of claim 7 wherein each lane image in the set of lane images includes a corresponding set of band images, and wherein the fitting the set of curves includes having computer executable logic determine movement amounts for moving towards band images for areas in the digital image, and wherein the first curve includes a set of control points, and wherein the local optimization includes having computer executable logic move the locations of the set of control points according to the movement amounts for areas of the digital image corresponding to the first curve.

9. The method of claim 7 wherein the fitting the set of curves includes having computer executable logic determine an approximate distance between adjacent lane images for areas of the digital image, and wherein the local optimization includes having computer executable logic move the first curve according to the determined approximate distance for areas corresponding to the first curve.

10. The method of claim 7 wherein the fitting the first curve includes having computer executable logic move the first curve according to a set of curvature limits on portions of the first curve.

11. The method of claim 7 wherein fitting the first curve includes having computer executable logic randomly perturb portions of the first curve during the local optimization.

12. The method of claim 7 wherein the fitting the first curve includes having computer executable logic ensure that the first curve does not cross adjacent curves of the set of curves.

13. The method of claim 1 wherein fitting the set of curves includes having computer executable logic perform a global optimization to fit the set of curves to the corresponding set of lane images.

14. The method of claim 13 wherein the global optimization includes having computer executable logic use a set of regularization rules to fit the set of curves to the corresponding different lane images.

15. The method of claim 14 wherein the set of regularization rules includes rules defining regularized spacing between curves of the set of curves and preferably curving of the first curve.

16. The method of claim 14 wherein the set of lane images have flow directions corresponding to the flows of the corresponding samples in the media, and wherein the set of regularization rules includes fitting the first curve to the direction of flow of lane images in regions near the first lane image.

17. The method of claim 13 wherein the global optimization includes having computer executable logic use a set of predetermined rules to fit the set of curves to the corresponding different lane images.

18. The method of claim 17 wherein the set of predetermined rules includes rules requiring the set of curves to have a generally gently curving shape.

19. The method of claim 17 wherein each sample in the set of samples includes sample material that will cause a bar code like appearance of the separated sample material in a corresponding lane, and wherein the set of predetermined rules includes rules requiring each curve of the set of curves to correspond to a single lane image having only a single bar code.

20. The method of claim 17 wherein the global optimization includes having computer executable logic reduce the error of the match of the set of curves to the corresponding different lane images.

21. The method of claim 20 wherein reducing the error of the match includes:
generating a new temporary position for at least a first curve in the set of curves;
using the new temporary position, determining whether the match of the set of curves to the corresponding set of lane images has improved;
if the match has improved, then making the position of the first curve equal to the new temporary position; and
if the match has not improved accepting the change with some probability as modified by "dynamic simulated annealing".

22. The method of claim 1 wherein the sample includes DNA sample material and fluorescent dyes, wherein the media includes a gel, and wherein the separated samples include the DNA sample material and the fluorescent dyes separated into bands.

23. The method of claim 1 wherein the sample includes DNA sample material and radioactive material, wherein the media includes a gel, and wherein the separated samples include the DNA sample material and the radioactive material separated into bands.

24. The method of claim 1 wherein the set of lanes of separated samples is derived from a thin layer chromatography process.

25. The method of claim 1 wherein the set of lanes of separated samples are formed by separating the sample based upon at least one characteristic of a set of characteristics of the sample, the set of characteristics including molecular size, charge, hydrophobicity, hydrophilicity, and structural rigidity.

26. The method of claim 1 wherein each curve in the set of curves is a spline.

27. A computer program product comprising:
a computer usable medium having a computer readable program code embodied therein for causing a computer to identify different lane images in a digital image, each lane image including a corresponding set of band image images the computer readable program code including,
program code for identifying the approximate centers of at least some band images of the set of band images,
program code for using the approximate centers to determine an approximate spacing between adjacent lane images of the different lane images,
program code for using the approximate spacing and the approximate centers to determine an initial set of curves, the initial set of curves representing an initial attempt at locating the different lane images in the digital image, and
program code for fitting the initial set of curves to the different lane images to generate a final set of curves, the final set of curves identifying the locations of the different lane images in the digital image.

28. The computer program product of claim 27 wherein the program code for using the approximate centers further includes a computer program implementation of a neural network, the neural network having been trained to identify the approximate centers of at least some band images for an input digital image, where the input digital image includes band images.

29. The computer program product of claim 27 wherein the program code fitting the initial set of curves includes program code for performing a cell automata process and a global optimization process.

30. A method of tracking different lane images in a digital image, the method comprising:

having computer executable logic use at least a sample image to train a pattern recognition system, the sample image including different sample lane images including sample features, the sample features corresponding to the identifying features;

having computer executable logic use the pattern recognition system to identify the identifying features in the different lane images;

having computer executable logic use the identifying features to determine an approximate set of curves to fit to the different lane images; and having computer executable logic generate a set of curves from the approximate set of curves by fitting the approximate set of curves to the different lane images, wherein the set of curves track the different lane images.

31. The method of claim 30 wherein the pattern recognition system includes a neural network including a finite impulse response filter, the finite impulse response filter having a set of coefficients that determine the response of the finite impulse response filter, and wherein using at least a sample image to train the pattern recognition system includes setting the set of coefficients.

32. The method of claim 30 wherein the identifying features include a set of bands, wherein each lane image of the set of lane images includes a corresponding set of bands.

33. The method of claim 32 wherein the sample features includes a set of sample bands, wherein each sample lane image includes a corresponding set of sample bands, and wherein using at least the sample image to train the pattern recognition system includes identifying the approximate centers of at least a subset of the set of sample bands.

34. The method of claim 30 wherein generating the set of curves includes performing a cell automata process for each curve in the approximate set of curves.

35. The method of claim 30 wherein generating the set of curves includes performing a global optimization process for each curve in the approximate set of curves.

36. A system for identifying different lanes of separated samples, the system comprising:

an apparatus for causing a set of samples to separate into different lanes of separated samples;

an image capture device to generate a digital image of the different lanes of separated samples, the digital image including a set of lane images, each lane image of the set of lane images corresponding to one of the different lanes; and a computer system which includes computer executable logic that receives the digital image and fits a set of curves to the different lane images.

37. The system of claim 36 wherein the apparatus includes a gel electrophoresis DNA sequencer.

38. The system of claim 36 wherein the image capture device includes a scanner, wherein the scanner is for scanning the set of lanes of separated samples, and wherein the image capture device is partially included in, and controlled by, the computer system.

* * * * *